United States Patent
Chaudry

(10) Patent No.: US 8,129,364 B2
(45) Date of Patent: Mar. 6, 2012

(54) FORMULATIONS AND METHODS FOR TREATING RHINOSINUSITIS

(75) Inventor: Imtiaz Chaudry, Napa, CA (US)

(73) Assignee: Dey Pharma, L.P., Basking Ridge, NJ (US)

( * ) Notice: Subject to any disclaimer, the term of this patent is extended or adjusted under 35 U.S.C. 154(b) by 0 days.

(21) Appl. No.: 11/250,925

(22) Filed: Oct. 14, 2005

(65) Prior Publication Data

US 2006/0051300 A1    Mar. 9, 2006

Related U.S. Application Data

(63) Continuation of application No. PCT/EP2004/003316, filed on Mar. 29, 2004, which is a continuation of application No. 10/657,550, filed on Sep. 4, 2003, which is a continuation-in-part of application No. 10/414,682, filed on Apr. 16, 2003, and a continuation-in-part of application No. 10/414,756, filed on Apr. 16, 2003, now Pat. No. 7,811,606.

(51) Int. Cl.
*A61K 9/00* (2006.01)
*A61K 9/12* (2006.01)
*A61K 9/14* (2006.01)
*A61K 31/56* (2006.01)

(52) U.S. Cl. .................. 514/177; 424/46; 424/489
(58) Field of Classification Search ............... 424/46, 424/489; 514/177
See application file for complete search history.

(56) References Cited

U.S. PATENT DOCUMENTS

| | | | |
|---|---|---|---|
| 3,091,569 A | 5/1963 | Sheffner | |
| 5,174,475 A | 12/1992 | Day et al. | |
| 5,593,688 A | 1/1997 | Baldeschwieler | |
| 5,858,330 A | 1/1999 | Boltri et al. | |
| 5,958,378 A * | 9/1999 | Waldrep et al. | 424/45 |
| 5,976,573 A | 11/1999 | Kim | |
| 5,993,781 A | 11/1999 | Snell et al. | |
| 6,113,894 A | 9/2000 | Smith | |
| 6,207,703 B1 | 3/2001 | Ponikau | |
| 6,241,969 B1 | 6/2001 | Saidi et al. | |
| 6,291,500 B2 | 9/2001 | Ponikau | |
| 6,368,616 B1 * | 4/2002 | Doi | 424/434 |
| 6,410,062 B1 | 6/2002 | Callaghan et al. | |
| 6,464,958 B1 * | 10/2002 | Bernini et al. | 424/43 |
| 6,465,709 B1 | 10/2002 | Sun et al. | |
| 6,509,028 B2 | 1/2003 | Williams et al. | |
| 6,555,566 B2 | 4/2003 | Ponikau | |
| 6,608,054 B2 * | 8/2003 | Meade et al. | 514/229.5 |
| 2001/0002404 A1 | 5/2001 | Webb et al. | |
| 2002/0006944 A1 | 1/2002 | Ohkawa et al. | |
| 2002/0010208 A1 | 1/2002 | Shashoua et al. | |
| 2002/0013331 A1 | 1/2002 | Williams et al. | |
| 2002/0052390 A1 | 5/2002 | Ponikau | |
| 2002/0061281 A1 * | 5/2002 | Osbakken et al. | 424/43 |
| 2002/0071874 A1 | 6/2002 | Olejnik et al. | |
| 2002/0124820 A1 | 9/2002 | Kreuter | |
| 2002/0136918 A1 | 9/2002 | Akutsu et al. | |
| 2002/0177609 A1 | 11/2002 | Swindell et al. | |
| 2002/0192288 A1 | 12/2002 | Williams et al. | |
| 2002/0198209 A1 | 12/2002 | Woodward et al. | |
| 2003/0017199 A1 | 1/2003 | Woodward et al. | |
| 2003/0065023 A1 | 4/2003 | Swindell et al. | |
| 2003/0222364 A1 * | 12/2003 | Jackson et al. | 264/5 |
| 2004/0045805 A1 | 3/2004 | Lancaster et al. | |
| 2004/0081626 A1 | 4/2004 | Watanabe et al. | |
| 2004/0136918 A1 * | 7/2004 | Garrett et al. | 424/46 |
| 2004/0141925 A1 | 7/2004 | Bosch et al. | |
| 2007/0140980 A1 * | 6/2007 | Capocchi et al. | 424/46 |
| 2008/0050442 A1 * | 2/2008 | Chaudry | 424/489 |

FOREIGN PATENT DOCUMENTS

| | | |
|---|---|---|
| EP | 0 343 268 | 11/1989 |
| EP | 0 385 445 A2 | 9/1990 |
| JP | 1-100120 A | 4/1989 |
| JP | 03-165833 | 7/1991 |
| JP | 5-506642 | 9/1993 |
| JP | 07-053358 | 2/1995 |
| JP | 11-130659 A | 5/1999 |
| JP | 11-514979 A | 12/1999 |
| JP | 2000-508675 A | 7/2000 |
| JP | 2001-002589 | 1/2001 |
| JP | 2001-520188 A | 10/2001 |
| JP | 2001-523638 | 11/2001 |
| JP | 2002-539154 | 11/2002 |
| JP | 2003-506396 | 2/2003 |
| JP | 2005-503378 | 2/2005 |
| JP | 2005-506369 | 3/2005 |
| WO | WO 86/03750 | 7/1986 |
| WO | WO 92/04365 * | 3/1992 |
| WO | WO 92/17183 | 10/1992 |
| WO | WO 97/08950 A1 | 3/1997 |
| WO | WO 99/18971 | 4/1999 |
| WO | WO 00/12063 A1 | 3/2000 |
| WO | WO 00/25746 | 5/2000 |

(Continued)

OTHER PUBLICATIONS

Lacy, C.; Armstrong, L. L.; Lipsy, R. J.; Lance, L. L. Drug Information Handbook, Lexi-Comp, Inc.: Cleveland, 1993, pp. 397.*
Merriam-Webster's Collegiate Dictionary, 10th edition, Merriam-Webster Incorporated: Springfield, Massachusetts, 1993, pp. 311.*
FLONASE® from the online Physician's Desk Reference (PDR®), accessed Dec. 1, 2007.*
BECONASE AQ® from the online Physician's Desk Reference (PDR®), accessed Nov. 19, 2007.*
1999-2000 Drug Information Handbook, Lacy, C.; Armstrong, L. L.; Armstrong, L. L.; Goldman, M. P.; Lance, L. L., Lexi-Comp, Inc.: Cleveland, 1999, pp. 12-114 and 445-446.*

(Continued)

*Primary Examiner* — James H. Alstrum-Acevedo
(74) *Attorney, Agent, or Firm* — Alston & Bird LLP

(57) ABSTRACT

The invention involves methods and formulations for treating or preventing rhinosinusitis, including fungus-induced rhinosinusitis in mammals. In one embodiment, the formulation of the present invention comprises a steroidal anti-inflammatory agent having a specific particle size distribution profile. The formulation may also comprise an antifungal agent, antibiotic or antiviral agent.

35 Claims, No Drawings

FOREIGN PATENT DOCUMENTS

| | | |
|---|---|---|
| WO | WO 00/27363 | 5/2000 |
| WO | WO 01/10409 A1 | 2/2001 |
| WO | WO 01/13885 A1 | 3/2001 |
| WO | WO 01/32125 | 5/2001 |
| WO | WO 01/49263 | 7/2001 |
| WO | WO 01/78743 A1 | 10/2001 |
| WO | WO 02/00199 | 1/2002 |
| WO | WO 02/055136 A2 | 7/2002 |
| WO | WO 02/072066 A1 | 9/2002 |
| WO | WO 03/013434 A2 | 2/2003 |
| WO | WO 03/020219 A2 | 3/2003 |
| WO | WO 03/035062 A1 | 5/2003 |

OTHER PUBLICATIONS

Lacy, C.; Armstrong, L. L.; Armstrong, L. L.; Goldman, M. P.; Lance, L. L., 1999-2000 Drug Information Handbook, Lexi-Comp, Inc.: Cleveland, 1999, pp. 26-28, 225-226, 453-456, and 721-722.*

Walker, S. "Management of allergic rhinitis", Nursing Times, 2003, 99(23), abstract.*

Hamuy, R. et al. "Topical antiviral agents for herpes simplex virus infections", Drugs Today, 1998, 34(12), abstract.*

Vippagunta et al. "Crystalline Solids," Advanced Drug Delivery Reviews, 2001, 48, pp. 3-26.*

Americas Family Physician—Jan. 1, 2001—Adult Rhinosinusitis: Diagnosis and Management—J. David Osguthorpe, M.D., Medical University of South Carolina, Charleston, South Carolina.

The Diagnosis and Incidence of Allergic Fungal Sinusitis—Jens U. Ponikau, MD; David A. Sherris, MD; Eugene B. Kern, MD; Henry A. Homburger, MD; Evangelos Frigas, MD; Thomas A. Gaffey, MD; and Glenn D. Robers, PhD—1999 Mayo Foundation for Medical Education and Research—May Clin. Proc, Sep. 1999, vol. 74.

Mayo Clinic, Rochester, Minnesota—Mayo Clinic Receives Patent for New Treatment of Chronic Sinus Infection Apr. 30, 2003.

NCBI—PubMed—Improved method for estimation of azole antifungal inhibitory concentrations against Candida Species, based on azole/antibiotic interactions; Odds FC, Abbot AB, Pye G., Troke PF.; Mar. 17, 2003.

Chervinsky, P., "Clinical Review of Once-Daily Beclomethasone Dipropionate for Seasonal Allergic Rhinitis", Clinical Therapeutics, 1996, 18(5), pp. 790-796.

Lacy et al., 1999-2000 Drug Information Handbook, Lexi-Comp, Inc., 1999, pp. 561-563 and 568-569.

Hebrecht et al., "Voriconazole versus amphotericin B for primary therapy of invasive aspergillosis", N.Eng. J. Med., 2002, 347(6), pp. 408-415.

Russian Office Action for Russian Application No. 2005 135 333 dated Sep. 18, 2009.

Comparison of Drug Particle Sizing of Innovator and Generic Nasal Spray Formulations Based on Raman Chemical Imaging. [online], [retrieved on Jan. 4, 2010]. Retrieved from the internet <www.chemimage.com/docs/white-papers/CI_Inhalation_ISPS_White_Paper.pdf>.

Waligorski et al., Raman Chemical Imaging of Complex Pharmaceutical Products. [online], [retrieved on Jan. 4, 2010]. Retrieved from the internet www.chemimage.com/docs/posters/Pharmaceutical/RCI_of_Complex_Pharmaceutical_Products.pdf>.

Bernstein, I. L., *Is the Use of Benzalkonium Chloride as a Preservative for Nasal Formulations a Safety Concern? A Cautionary Note Based on Compromised Mucociliary Transport*, J. Allergy Clin. Immunol., 105(1), Jan. 2000, pp. 39-44.

Office Action dated Jul. 12, 2010, and issued in connection with corresponding Canadian Application No. 2,522,294 (Our Ref: 340938).

Office Action mailed Aug. 6, 2010, and issued in connection with corresponding U.S. Appl. No. 10/657,550 (Our Ref: 277062).

Parikh, A., et al.; Topical corticosteroids in chronic rhinosinusitis: a randomized, double-blind, placebo-controlled trial using fluticasone propionate aqueous nasal spray; Rhinology, 39; 2001; pp. 75-79.

Office Action for Japanese Application No. 2006-504903 dated Aug. 4, 2010.

Office Action for Japanese Application No. 2006-504901 dated Aug. 4, 2010.

Office Action for Japanese Application No. 2006-504902 dated Aug. 4, 2010.

Office Action for Japanese Application No. 2006-516000 dated Sep. 8, 2010.

* cited by examiner

FORMULATIONS AND METHODS FOR TREATING RHINOSINUSITIS

CROSS REFERENCE TO RELATED APPLICATIONS

The present application is a continuation of PCT/EP2004/003316, filed Mar. 29, 2004, which is a continuation of U.S. application Ser. No. 10/657,550, filed Sept. 4, 2003, which is a continuation-in-part of U.S. application Ser. No. 10/414,682 and U.S. application Ser. No. 10/414,756, both of which were filed Apr. 16, 2003 now U.S. Pat. No. 7,811,606 and are incorporated herein by reference in their entirety.

FIELD OF THE INVENTION

The present invention relates to formulations and methods for treating rhinosinusitis in mammals (e.g., humans), including but not limited to fungus induced rhinosinusitis. The formulations of the present invention comprise a steroidal agent, such as fluticasone or beclomethasone, wherein the steroidal agent has a specific particle size distribution profile. The formulations may also comprise an antibiotic, antifungal agent or an antiviral agent, or any combination thereof. While the formulations of the present invention may take any form, preferably they are provided as a sterile, aqueous suspension or solution which can be administered intranasally to the nasal-paranasal mucosa via spray pump. Also, the steroidal agent may be administered alone or in conjunction with an antifungal agent, antibiotic or antiviral agent.

BACKGROUND OF THE INVENTION

Rhinosinusitis is generally described as an inflammation of the nasal cavity and/or paranasal sinuses and involves the nasal mucosa. Chronic rhinosinusitis (CRS) is diagnosed when signs or symptoms of inflammation persist for 8-12 weeks or longer. It is estimated that one out of every seven Americans suffers from chronic rhinosinusitis (CRS). Symptoms of CRS include nasal obstruction, loss of sense of smell, nasal or postnasal discharge, nasal congestion, and facial pain/pressure (typically over the affected sinus area).

CRS impairs normal physical and social functioning, and patients with CRS typically suffer from an overall poor quality of life. Moreover, CRS is often associated with other co-morbid conditions such as asthma, eczema and other media. Asthma is found in 20-35% of patients with CRS, and CRS is found in up to 75% of moderate-to severe asthmatics.

It is now known that rhinosinusitis may be caused by fungi found in mucus. It is believed that some persons have an immunologic response to certain fungi found in most, if not all, persons' mucus. This immunologic response causes activated white blood cells, eosinophils, to enter the mucus. The activated eosinophils release a major basic toxic protein into the mucus which attacks and kills the fungi, but damages the nose and sinus membranes as well. The major basic protein also injures the epithelium, which allows bacteria to infect the tissues.

One type of fungus-induced rhinosinusitis is allergic fungus rhinosinusitis (AFS). AFS is generally diagnosed by: (1) the presence of nasal polyps; (2) allergic mucin; (3) CRS evidenced by CT scan; (4) positive fungal culture or histology; and/or (5) allergy to fungi by history, skin prick test or serology. AFS often leads to or is associated with CRS.

Current treatments for fungus induced rhinosinusitis include antifungal medications to remove the antigenic burden. A topical or systemic corticosteroid may also be prescribed to control inflammation of the mucosal tissue associated with CRS. This inflammation is thought to contribute to tissue and bone destruction associated with CRS. Recently, it has been discovered that steroidal anti-inflammatories such as fluticasone propionate (FP) and beclomethasone dipropionate (BDP) having a particular particle size distribution profile provide increased bioavailability, increased efficacy and/or prolonged therapeutic effect when administered intranasally.

CRS may also be characterized by or associated with a chronic bacterial infection of the sinuses (nasal-paranasal region) which is often superimposed upon a self-perpetuating, eosinophil-rich inflammatory process in the sinuses. Currently, antibiotic therapy is indicated for up to six weeks or more for the treatment and elimination of the bacterial infection associated with CRS.

SUMMARY OF INVENTION

The present invention relates generally to formulations and methods for treating rhinosinusitis in mammals (e.g., humans), including, but not limited to fungus-induced rhinosinusitis. In one embodiment, the formulations of the present invention comprise a steroid, alone or in combination with an antifungal agent or antibiotic. It is believed that treating the patient with an antifungal agent will sufficiently reduce the level of fungal organisms in the patient's mucus such that the one ore more of the symptoms of rhinosinusitis are prevented from developing, or are lessened, or are prevented from worsening.

In an embodiment, the present formulations comprise about 4 mg to about 30 mg of the anti-fungal agent amphotericin $\beta$. In an alternative embodiment, the formulation of the present invention comprises about 20 to about 70 mg of the anti-fungal agent fluconazole or itraconazole.

The present invention is also based on the realization that a patient or individual may have already developed one or more symptoms of rhinosinusitis, possibly CRS, when he or she first seeks the help of a physician or by the time that treatment is started. Thus, it would also be beneficial to provide an anti-inflammatory steroid to the patient to treat inflammation of the mucosal tissue associated with rhinosinusitis, since such inflammation might lead to or contribute to tissue and bone destruction in the nasal-paranasal region.

It has recently been discovered that certain steroidal anti-inflammatories having a specific particle size distribution profile provide increased bioavailability, increased efficacy or prolonged therapeutic effect when administered intranasally. In one embodiment, the formulation of the present invention comprises about 25 to about 400 mcg of the steroidal anti-inflammatory agent, including but not limited to, fluticasone, or a pharmaceutically acceptable derivative thereof, having the following particle size distribution profile: about 10% of the drug substance particles have a particle size of about 0.90 microns; about than 25% of the drug substance particles have a particle size of less than 1.6 microns; about 50% of the drug substance particles have a particle size of less than 3.2 microns; about 75% of the drug substance particles have a particle size of less than 6.10 microns; about 90% of the drug substance particles have a particle size of less than 10.0 microns.

In an alternative embodiment, the formulation of the present invention comprises about 0.2 to about 3 mg of the steroidal anti-inflammatory beclomethasone, or a pharmaceutically acceptable derivative thereof, having the following particle size distribution profile: about 10% of the drug substance particles have a particle size of about 0.75 microns;

about than 25% of the drug substance particles have a particle size of less than 1.5 microns; about 50% of the drug substance particles have a particle size of less than 2.0 microns; about 75% of the drug substance particles have a particle size of less than 3.5 microns; about 90% of the drug substance particles have a particle size of less than 5.0 microns; and, greater than 90% or about 100% of the drug substance particles have a particle size of less than 10 microns.

In many instances the fungus-induced rhinosinusitis may be accompanied by, or associated with, a bacterial infection of the nasal-paranasal mucosa. In one embodiment, the formulations of the present invention comprise an antibiotic. In an alternative embodiment, the present formulations comprise about 1 to about 800 mg of the antibiotic neomycin sulfate.

The formulations of the present invention may be provided in any form which directly contacts the formulation with the nasal-paranasal mucosa. In one embodiment, the present formulation is provided as a sterile aqueous solution or suspension. In an alternative embodiment, the formulation is in a metered dose spray pump.

The present invention also generally relates to methods for treating rhinosinusitis, including fungus-induced rhinosinusitis. In one alternative embodiment, an individual suffering from rhinosinusitis may be administered a steroidal agent of the present invention alone, or in combination or conjunction with an anti-fungal agent, antibiotic or antiviral agent. For example, the steroidal agent may be administered separately from the anti-fungal agent or antibiotic, or each of these ingredients may be administered simultaneously (e.g., in a single formulation) or individually, concurrently, in tandem or subsequently relative to each other, or in any combination thereof.

DETAILED DISCUSSION OF THE INVENTION

The present invention is directed to formulations for the treatment of one or more symptoms of rhinosinusitis in an individual. Rhinosinusitis occurs in the nasal-paranasal region. Symptoms of rhinosinusitis include, without limitation, facial pain, pressure, and/or fullness; loss of smell; nasal obstruction or blockage; nasal or postnasal discharge; rhinorrhea; hyposimia/ansomnia; fever; headaches; halitosis; fatigue; dental pain; cough; and ear pain, pressure, and/or fullness. Upon examination, the presence of thick mucus or the visual identification of nasal or paranasal obstruction with mucus or polyps often indicates a rhinosinusitis condition.

Nasal polyps may also be associated with or indicative of rhinosinusitis. Nasal polyps are outgrowths from the nasal-paranasal mucosa that are typically smooth, gelatinous, semi-translucent, round or pear shaped, and pale. In general, nasal polyps are located on the lateral wall of the nose, usually in the middle meatus or along the middle and superior turbinates. Most nasal polyps arise from the ethmoid sinus but some polyps originate in the maxillary sphenoid sinuses. The mass of a nasal polyp is composed mainly of edematous fluid with sparse fibrous cells and a few mucous glands. The surface epithelium of nasal and paranasal polyps generally reveals squamous metaplasia. Eosinophils are usually present in polyps in moderate to large numbers, and it is now known that nasal polyp fluid contains greater than normal concentrations of IgA, IgE, IgG, and IgM antibodies as well as abnormally high concentrations of IL-5, a cytokine that contributes to eosinophil activation and survival.

It is understood that the scope of the invention is directed to the treatment of rhinosinusitis including, but not limited to, any rhinosinusitis condition, including, but not limited to, acute, subacute, recurrent acute and chronic rhinosinusitis, which may be accompanied by, aggravated by, associated with or caused by (in whole or in part) fungi, viruses, or microorganisms in the mucosa. For example, rhinosinusitis may include fungus-induced rhinosinusitis caused by, for example, an immunologic response to mucosal fungi or other organism. In one alternative embodiment, the fungus-induced rhinosinusitis is allergic fungal rhinosinusitis, or AFS.

Formulation

In one alternative embodiment, the present invention is directed to formulations for the treatment of rhinosinusitis. In one embodiment, the formulations comprise a steroidal anti-inflammatory, alone or in combination with an antifungal agent, antibiotic or antiviral agent. As used herein, treatment means the prophylaxis, prevention or amelioration of one or more symptoms of, or associated with, rhinosinusitis, or any manner in which one or more of the symptoms of, or associated with, rhinosinusitis are beneficially altered or are prevented from worsening. As used herein, amelioration means any lessening, whether permanent or temporary, lasting or transient, of one or more symptoms of rhinosinusitis, including but not limited to fungus-induced rhino sinusitis.

Antifungal Agent

Antifungal agents for use herein include any agent effective in treating rhinosinusitis, including fungus-induced rhinosinusitis. Preferably, the antifungal agent of the present formulations reduces the presence of fungal organisms within mucus to a level such that the characteristic inflammatory responses and resulting damages associated with fungal induced rhinosinusitis are lessened, whether permanent or temporary, lasting or transient, stopped, treated, or prevented.

For example, in one alternative embodiment of the present invention, an antifungal agent for use herein may include any agent that prevents the growth of or kills a fungal organism such as antifungal polyene macrolides, tetraene macrolides, pentaenic macrolides, fluorinated pyrimidines, imidazoles, triazoles, azoles, halogenated phenolic ethers, thiocarbamates, and allylamines, and other. In addition, antifungal agents can be agents that interpolate fungal cell wall components or act as sterol inhibitors. Specific antifungal agents within the scope of the invention include, without limitation, amphotericin $\beta$, flucytosine, ketoconazole, miconazole, itraconazole, fluconazole, griseofulvin, clotrimazole, econazole, terconazole, butoconazole, oxiconazole, sulconazole, saperconazole, voriconazole, ciclopirox olamine, haloprogin, tolnaftate, naftifine, nystatin, natamycin, terbinafine hydrochloride, morpholines, butenafine undecylenic acid, Whitefield's ointment, propionic acid, and caprylic acid as well as those agents that can be identified as antifungal agents using methods well known in the art. Preferably, the antifungal agent of the present formulations is amphotericin $\beta$ or fluconazole.

It is noted that a particular patient may possess a fungal organism acting as the etiological agent that is resistant to a particular antifungal agent. In such a case, an embodiment of this invention involves treating that patient with an effective antifungal agent (e.g., an antifungal agent that prevents the growth of, or kills, the fungal organism acting as the etiological agent). Such fungal organisms acting as etiological agents can be identified using collection and culture methods known in the art.

In one alternative embodiment, the formulation of the present invention may comprise any amount of antifungal agent that reduces, prevents, or eliminates one or more symptoms of, or associated with, fungus-induced rhinosinusitis without producing significant toxicity. In one embodiment, an effective amount may be any amount greater than or equal to the minimum inhibitory concentration (MIC) for a fungal organism or isolate present within a particular individual's mucus that does not induce significant toxicity to the individual upon administration. Some antifungal agents may have a relatively large concentration range that is effective while others may have a relatively narrow effective concentration range. In addition, the effective amount can vary depending upon the specific fungal organism or isolate since certain organisms and isolates are more or less susceptible to particular antifungal agents. Such effective amounts can be determined for individual antifungal agents using commonly available or easily ascertainable information involving antifungal effectiveness concentrations, animal toxicity concentrations, and tissue permeability rates.

For example, non-toxic antifungal agents typically can be directly or indirectly administered in any amount that exhibits antifungal activity within mucus. In addition, antifungal agents that do not permeate mucosal epithelium typically can be directly administered to the mucus in any amount that exhibits antifungal activity within mucus. Using the information provided herein, such effective amounts also can be determined by routine experimentation in vitro or in vivo. For example, a patient having a fungus-induced rhinosinusitis can receive direct administration of an antifungal agent in an amount close to the MIC calculated from in vitro analysis. If the patient fails to respond, then the amount can be increased by, for example, ten fold. After receiving this higher concentration, the patient can be monitored for both responsiveness to the treatment and toxicity symptoms, and adjustments made accordingly.

In one embodiment, the present formulations comprise about 0.01 ng to about 1000 mg per kg of body weight of the mammal per administration of formulation, where the formulation is administered directly to the nasal-paranasal mucose. Antifungal agent particularly suitable for administration are itraconazole, ketoconazole, or voriconazole. The MIC values for voriconazole range from about 0.003 .mu.g/mL to about 4 .mu.g/mL depending upon the specific fungal organism or isolate tested. For fluconazole, the MIC values range from about 0.25 .mu.g/mL to greater than about 64 .mu.g/mL.

Various factors can influence the actual amount of antifungal agent in the formulations provided herein. For example, the frequency of administration of the formulations, duration of treatment, combination of other antifungal agents, site of administration, degree of inflammation, and the anatomical configuration of the treated area may require an increase or decrease in the actual amount of antifungal agent in the present formulations.

Table 1 sets forth preferable ranges and dosages of the antifungal agent of the present invention.

In one alterative embodiment, the steroidal anti-inflammatory agents have a specific particle size distribution profile. As used herein, particle size refers to an average particle size as measured by conventional particle size measuring techniques well known to those skilled in the art, such as, for example, sedimentation field flow fractionation, photon correlation spectroscopy, or disk centrifugation, among other techniques.

Fluticasone

Preferably, the intranasal steroid of the present formulations is fluticasone propionate. Fluticasone propionate is a synthetic corticosteroid and has the empirical formula $C_{25}H_{31}F_3O_5S$. It has the chemical name S-(fluromethyl)6$\alpha$, 9-difluoro-11$\beta$-17-dihydroxy-16$\alpha$-methyl-3-oxoandrosta-1, 4-diene-17$\beta$-carbothioate, 17-propionate. Fluticasone propionate is a white to off-white powder with a molecular weight of 500.6 and is practically insoluble in water, freely soluble in dimethyl sulfoxide and dimethylformamide, and slightly soluble in methanol and 95% ethanol.

In one embodiment, the formulation of the present invention is an aqueous suspension comprising about 0.005% to about 5%, or about 0.01% to about 2.5%, or about 0.01% to about 0.2%, or about 0.01% to about 0.1%, or about 0.1% to about 0.75% by weight of a drug substance. In a preferred embodiment, the formulation is an aqueous suspension comprising about 0.025% to about 1.0% of a drug substance, wherein the drug substance is preferably fluticasone. Even more preferably, the formulation is an aqueous suspension comprising about 0.04% to about 0.06% by weight of a drug substance wherein the drug substance is preferably fluticasone propionate. In a preferred embodiment, the formulation of the present invention is an aqueous suspension comprising about 0.045% by weight of fluticasone propionate, wherein the fluticasone propionate has the following particle size distribution profiles disclosed herein.

In an embodiment, the formulations of the present invention may comprise a steroidal anti-inflammatory (e.g., fluticasone propionate) having the following particle size distribution profile: about 10% or less of the steroid particles have a particle size of less than 0.90 microns; about 25% or less of the steroid particles have a particle size of less than 1.6 microns; about 50% or less of the steroid particles have a particle size of less than 3.2 microns; about 75% or less of the steroid particles have a particle size of less than 6.10 microns; about 90% or less of the steroid particles have a particle size of less than 10 microns.

TABLE 1

Antifungal Agents and Dosages

| Generic Name | Brand Name | Class | Preferable Range | More Preferable Range | Most Preferable Range | Most Preferable Dose |
| --- | --- | --- | --- | --- | --- | --- |
| Amphotericin β | Fungizone | Antifungal | 0.5-150 mg | 4-30 mg | 7.5-15 mg | 10 mg Q12H |
| Fluconazole | Diflucan | Antifungal | 0.5-150 mg | 20-70 mg | 25-50 mg | 10 mg Q12H |
| Itraconazole | Sporanox | Antifungal | 0.5-150 mg | 20-70 mg | 25-50 mg | 30 mg Q12H |

Steroidal Anti-Inflammatory

Steroidal anti-inflammatories for use herein include fluticasone, beclomethasone, any pharmaceutically acceptable derivative thereof, and any combination thereof. As used herein, a pharmaceutically acceptable derivative includes any salt, ester, enol ether, enol ester, acid, base, solvate or hydrate thereof. Such derivatives may be prepared by those of skill in the art using known methods for such derivatization.

In an alternative embodiment, the formulation of the present invention comprises a steroidal anti-inflammatory having the following particle size distribution profile: about 10% of the steroid particles have a particle size of less than 0.70 microns; about 25% of the steroid particles have a particle size of less than 1.30 microns; about 50% of the steroid particles have a particle size of less than 2.5 microns; about 75% of the steroid particles have a particle size of less than 4.0 microns; about 90% of the steroid particles have a particle size of less than 6.0 microns; and greater than 90% or about 100% of the steroid particles have a particle size of less than 10 microns. Preferably, the steroid is fluticasone propionate.

In one preferred embodiment, the formulation of the present invention comprises a steroid having the following particle size distribution profile: about 10% of the steroid particles have a particle size less than 0.50 microns; about 25% of the steroid particles have a particle size less than 0.90 microns; about 50% of the steroid particles have a particle size less than 1.7 microns; about 75% of the steroid particles have a particle size less than 3.5 microns; about 90% of the steroid particles have a particle size less than 5.5 microns.

In another alternative embodiment, greater than 90% or about 100% of the steroid particles have a particle size less than 15 microns, preferably less than 10 microns, more preferably less than 8 microns, most preferably less than 7 microns. In yet another alternative embodiment, about 10% of the steroid particles have a particle size of less than 0.40microns; about 25% of the steroid particles have a particle size of less than 0.80 microns; about 50% of the steroid particles have a particle size of less than 1.60 microns; about 75% of the steroid particles have a particle size of less than 3.0 microns; about 90% of the steroid particles have a particle size of less than 5.30 microns and greater than 90% or about 100% of the steroid particles have a particle size of less than 10 microns.

Beclomethasone

Also preferably, the steroidal anti-inflammatory of the present formulations is beclomethasone dipropionate or its monohydrate. Beclomethasone dipropionate has the chemical name 9-chloro-11b,17,21-trih-ydroxy-16b-methylpregna-1,4-diene-3,20-doine17,21-dipropionate. The compound may be a white powder with a molecular weight of 521.25; and is very slightly soluble in water (Physicians' Desk Reference.RTM), very soluble in chloroform, and freely soluble in acetone and in alcohol.

In one embodiment, the formulation of the present invention is an aqueous suspension comprising about 0.005% to about 5%, or 0.01% to about 2.5% w/w of a drug substance, calculated on a dry basis. In a preferred embodiment, the formulation is an aqueous suspension comprising about 0.025% to about 1.0% w/w of a drug substance, calculated on a dry basis having the particular particle size distribution profile of the present invention, wherein the drug substance is preferably beclomethasone. Even more preferably, the formulation is an aqueous suspension comprising about 0.04% to about 0.05% w/w of a drug substance, calculated on a dry basis. In a preferred embodiment, the drug substance is beclomethasone dipropionate.

In one preferred embodiment, the formulation of the present invention is an aqueous suspension comprising about 0.042% by weight of beclomethasone dipropionate, calculated on a dry basis, wherein the beclomethasone dipropionate has the following particle size distribution range: about 10% of the particles have a particle size of less than 0.35 microns; about 25% of the particles have a particle size of less than 0.65 microns; about 50% of the particles have a particle size of less than 1.20 microns; about 75% of the particles have a particle size of less than 1.9 microns; about 90% of the particles have a particle size of less than 2.85 microns; and greater than 90% or about 100% of the particles have a particle size of less than 6.0 microns.

The formulations of the present invention may comprise a steroidal anti-inflammatory (e.g., beclometasone diproprionate) having the following particle size distribution profile: about 10% or less of the steroid particles have a particle size of less than 0.75 microns; about 25% or less of the steroid particles have a particle size of less than 1.5 microns; about 50% or less of the steroid particles have a particle size of less than 2.0 microns; about 75% or less of the steroid particles have a particle size of less than 3.5 microns; about 90% or less of the steroid particles have a particle size of less than 5.0 microns; and greater than 90% or about 100% of the steroid particles have a particle size of less than 10 microns.

In an alternative embodiment, the formulation of the present invention comprises a steroidal anti-inflammatory having the following particle size distribution profile: about 10% of the steroid particles have a particle size of less than 0.35 microns; about 25% of the steroid particles have a particle size of less than 0.70 microns; about 50% of the steroid particles have a particle size of less than 1.25 microns; about 75% of the steroid particles have a particle size of less than 2.0 microns; about 90% of the steroid particles have a particle size of less than 3.0 microns; and greater than 90% or about 100% of the steroid particles have a particle size of less than 6.5 microns. Preferably, the steroid is beclomethasone dipropionate.

In one preferred embodiment, the formulation of the present invention comprises a steroidal anti-inflammatory having the following particle size distribution profile: about 10% of the steroid particles have a particle size less than 0.40 microns; about 25% of the steroid particles have a particle size less than 0.70 microns; about 50% of the steroid particles have a particle size less than 1.3 microns; about 75% of the steroid particles have a particle size less than 2.0 microns; about 90% of the steroid particles have a particle size less than 3.0 microns; greater than 90% or about 100% of the steroid particles have a particle size less than 6.0 microns.

In another alternative embodiment, the formulation of the present invention comprises a steroidal anti-inflammatory having the following particle size distribution profile: about 10% of the steroid particles have a particle size less than 0.60 microns; 25% of the steroid particles have a particle size less than 0.90 microns; about 50% of the steroid particles have a particle size less than 1.5 microns; about 75% of the steroid particles have a particle size less than 2.5 microns; about 90% of the steroid particles have a particle size less than 3.5 microns; greater than 90% or about 100% of the steroid particles have a particle size less than 6.0 microns.

In another alternative embodiment, greater than 90% or about 100% of the steroid particles have a particle size less than 15 microns, preferably less than 10 microns, more preferably less than 8 microns, most preferably less than 7 microns. In another preferred embodiment, greater than 90% or about 100% of the steroid particles have a particle size between 4 and 7 microns or 5 and 6 microns. In another embodiment, greater than 90% or about 100% of the steroid particles have a particle size less than 10 microns, preferably less than 7 microns; less than 6 microns; less than 5 microns, or less than 4 microns.

Providing steroidal anti-inflammatories according to the present invention is believed to be a more effective way to provide the medication to the nasal-paranasal region, thereby increasing bioavailability and efficacy of the steroid. It is understood that each of the particle size distribution profiles described in application Ser. Nos. 10/414,682 and 10/414,756 may be suitable for any of the anti-inflammatory agents described herein. The preferred anti-inflammatory agents are fluticasone and beclomethasone. Also, the dosages described in these applications may also be suitable for use in the present invention. Each of these applications are incorporated herein by reference in their entirety.

Additionally, the formulations of the present invention may comprise fluticasone or beclomethasone alone or in combination with one or more other steroidal anti-inflammatories. Examples of steroidal anti-inflammatories for use herein include, but are not limited to, betamethasone, triamcinolone, dexamethasone, prednisone, mometasone, flunisolide and budesonide. Other anti-inflammatory for use herein are listed below in Table 2.

TABLE 2

Steroidal Anti-inflammatory Agents and Dosages

| Generic Name | Brand Name | Class | Preferable Range | More Preferable Range | Most Preferable Range | Most Preferable Dose |
|---|---|---|---|---|---|---|
| Acetylcysteine | Mucomist Mucosil | Mucolytics | 125-500 mg | 150-450 mg | 200-400 mg | 300 mg Q12H |
| Amikacin | Amikin | Aminoglycoside | 50-500 mg | 75-300 mg | 100-200 mg | 166 mg Q8-12H |
| Amphotericin B | Fungizone | Antifungal | 2.5-45 mg | 4-30 mg | 7.5-15 mg | 10 mg Q12H |
| Atropine | | Anticolinergic | 10-700 mcg | 25-400 mcg | 75-30 mcg | 200 mcg Q12H |
| Azelastine | Astelin | Antihistamine | 137-1096 mcg | 204-822 mcg | 382-616 mcg | 411 mcg Q12H |
| Azithromycin | Zithromax | Macrolide | 50-400 mg | 75-300 mg | 150-200 mg | 167 mg Q12H |
| Aztreonan | Azactam | Monobactam | 250-1000 mg | 300-900 mg | 475-750 mg | 450 mg Q8H |
| Beclamethasone | Vanceril Beclovent | Steroidal Anti-inflammatory | 0.1-4 mg | 0.2-3 mg | 0.2-2 mg | 0.8 mg Q12H |
| Betamethasone | Celestone | Steroidal Anti-inflammatory | 0.1-4 mg | 0.2-3 mg | 0.2-2 mg | 0.8 mg Q12H |
| Cefazolin | Ancef, Kefzol | Cephlasporin (Gen I) | 250-1000 mg | 300-900 mg | 575-700 mg | 650 mg Q8H |
| Cefepine | Maxipime | Cephlasporin (Gen IV) | 125-1000 mg | 200-900 mg | 575-700 mg | 650 mg Q12H |
| Cefonicid | Moniacid | Cephlasporin (Gen II) | 250-1000 mg | 300-900 mg | 575-700 mg | 600 mg Q24H |
| Cefaperazone | Cefobid | Cephlasporin (Gen III) | 250-1000 mg | 300-900 mg | 575-700 mg | 600 mg Q12H |
| Cefotaxime | Claforan | Cephlasporin (Gen III) | 250-1000 mg | 300-900 mg | 575-700 mg | 600 mg Q8-12H |
| Cefotetan | Cefotan | Cephlasporin (Cephamycin) | 250-1000 mg | 300-900 mg | 575-700 mg | 600 mg Q8-12H |
| Cefoxitin | Mefoxin | Cephlasporin (Cephamycin) | 250-1000 mg | 300-900 mg | 575-700 mg | 600 mg Q12H |
| Ceftazidime | Fortaz, Ceptaz | Cephlasporin (Gen III) | 250-1000 mg | 300-900 mg | 475-750 mg | 550 mg Q12H |
| Ceftizoxime | Cefizox | Cephlasporin (Gen III) | 250-1000 mg | 300-900 mg | 575-700 mg | 600 mg Q8-12H |
| Ceftriaxone | Rocephin | Cephlasporin (Gen III) | 250-1000 mg | 300-900 mg | 575-700 mg | 650 mg Q12H |
| Cefuroxime | Ceftin | Cephlasporin (Gen II) | 100-600 mg | 200-520 mg | 250-400 mg | 285 mg Q8H |
| Cephapirin | Cefadyl | Cephlasporin (Gen I) | 250-1000 mg | 300-900 mg | 575-700 mg | 650 mg Q12H |
| Ciprofloxacin | Cipro | Quinolone | 25-200 mg | 50-175 mg | 75-110 mg | 90 mg Q12H |
| Clindamycin | Cleocin | Lincosamide | 50-600 mg | 75-500 mg | 125-300 mg | 225 mg Q12H |
| Cromolyn Sodium | Intal/Nasalcrom | Mast cell stabilizer | 5-100 mg | 7.5-75 mg | 10-50 mg | 20 mg Q12H |
| Dexamethasone | Decadron | Steroidal Anti-inflammatory | 0.1-4 mg | 0.2-3 mg | 0.2-2 mg | 0.8 mg Q12H |
| Dornase alpha | Pulmozyme | Mucolytic | 0.5-5 mg | 1-4 mg | 2-3 mg | 1.5 mg Q12H |
| Doxycycline | Vibramycin | Tetracycline | 10-100 mg | 15-80 mg | 25-65 mg | 27 mg Q12H |
| Erythromycin Lactobionate | Erythrocin | Macrolide | 50-600 mg | 60-350 mg | 100-300 mg | 150 mg Q8H |
| Fluconazole | Diflucan | Antifungal | 12.5-150 mg | 20-70 mg | 25-50 mg | 30 mg Q12H |
| Flunisolide | Aerobid Nasalide | Steroidal Anti-inflammatory | 0.1-4 mg | 0.2-3 mg | 0.2-2 mg | 0.8 mg Q12H |
| Flurbiprofen | Ocufen | Nonsteroidal Anti-inflammatory | 0.01-2 mg | 0.05-1 mg | 0.1-0.5 mg | 0.15 mg Q12H |
| Fluticasone | Flonase | Steroidal Anti-inflammatory | 10-700 mcg | 25-400 mcg | 75-300 mcg | 200 mcg Q24H |
| Gentamycin | Garamycin | Aminoglycoside | 10-200 mg | 30-150 mg | 80-120 mg | 95 mg Q8-12H |
| Ibuprofen | Motrin | Nonsteroidal Anti-inflammatory | 25-400 mg | 30-300 mg | 50-150 mg | 100 mg Q12H |
| Ipratropium | Atrovent | Anticholinergic | 10-700 mcg | 25-400 mcg | 75-300 mcg | 200 mcg Q12H |
| Itraconazole | Sporanox | Antifungal | 12.5-150 mg | 20-70 mg | 25-50 mg | 30 mg Q12H |
| Ketorolac | Acular | Nonsteroidal Anti-inflamattory | 0.05-4 mg | 0.1-2 mg | 0.3-1 mg | 0.5 mg Q12H |
| Levofloxacin | Levaquin | Quinolone | 40-200 mg | 50-150 mg | 60-80 mg | 70 mg Q12H |
| Linezolid | Zyvox | Miscellaneous anti-bacterial | 50-600 mg | 75-450 mg | 100-300 ng | 200 mg Q12H |
| Loratidine | Claritin | Antihistamine | 0.5-10 mg | 1-7.5 mg | 1-5 mg | 2 mg Q12H |
| Meropenem | Merrin | Carbapenem | 200-75 mg | 250-700 mg | 300-500 mg | 33 mg Q8H |
| Mezlocillin | Mezlin | Penicillin | 300-1500 mg | 375-1000 mg | 750-950 mg | 833 mg Q6H |
| Miconazole | Monistat | Antifungal | 12.5-300 mg | 30-200 mg | 50-100 mg | 60 mg Q12H |
| Montelukast | Singulair | Antileukotriene | 0.5-15 mg | 2-25 mg | 3-15 mg | 10 mg Q12H |

TABLE 2-continued

Steroidal Anti-inflammatory Agents and Dosages

| Generic Name | Brand Name | Class | Preferable Range | More Preferable Range | Most Preferable Range | Most Preferable Dose |
|---|---|---|---|---|---|---|
| Mupirocin | Bactroban | Antibacterial | 1-25 mg | 1.5-20 mg | 2-15 mg | 10 mg Q6-8H |
| Nafcillin | Unipen | Penicillin | 250-1000 mg | 300-900 mg | 575-700 mg | 600 mg Q8H |
| Nedocromil | Tilade | Mast cell stabilizer | 1-25 mg | 3-15 mg | 5-12 mg | 7 mg Q12H |
| Ofloxacin | Floxin | Quinolone | 25-200 mg | 50-175 mg | 75-110 mg | 90 mg Q12H |
| Oxacillin | Prostaphin | Penicillin | 250-1000 mg | 300-900 mg | 575-700 mg | 600 mg Q8H |
| Oxymetazoline | Afrin | Decongestant | 0.05-0.5 mg | 0.075-0.4 mg | 0.1-0.3 mg | 0.2 mg Q12H |
| Phenylepherine | Neo-Synephine | Decongestant | 5-50 mg | 10-35 mg | 15-20 mg | 10 mg Q12H |
| Piperacillin | Pipracil | Penicillin | 100-1000 mg | 125-750 mg | 250-600 mg | 460 mg Q6H |
| Potassium Iodide | — | Antiseptic | 30-200 mg | 40-150 mg | 50-80 mg | 60 mg Q12H |
| Rifampin | Rifadin | Miscellaneous | 500-5000 mg | 1000-4000 mg | 1500-3500 mg | 2250 mg Q12H |
| Taurolin | Taurolidine | Non antibiotic antimicrobial | 5-200 mg | 20-150 mg | 40-120 mg | 80 mg Q12H |
| Tetrahydrozolidine | Tizine | Decongestant | 0.05-0.5 mg | 0.06-0.4 mg | 0.1-0.3 mg | 0.15 mg Q12H |
| Ticarcillin + Clavulanate | Timentin | Penicillin | 500-5000 mg | 1000-4000 mg | 1500-3500 mg | 2250 mg Q6-8H |
| Tobramycin | Nebcin | Aminoglycoside | 10-200 mg | 30-150 mg | 80-120 mg | 95 mg Q8-12H |
| Triamcinalone | Asthmacor Aristocort | Steroidal Anti-inflammatory | 0.05-3 mg | 0.2-2.5 mg | 0.5-2 mg | 0.6 mg Q12H |
| Vancomycin | Vancocin | Antibiotic-miscellaneous | 50-400 mg | 75-325 mg | 125.250 mg | 166 mg Q6-8H |
| Xylometazoline | Otrivin | Decongestant | 0.05-0.4 mg | 0.075-03 mg | 0.1-0.2 mg | 0125 mg Q12H |
| Zafirlukast | Accolate | Antileukotriene | 2-60 mg | 4-50 mg | 6-30 mg | 20 mg Q12H |

Antibiotic

The formulations of the present invention may further comprise an antibiotic. Additionally, since more than one bacterial organism may be associated with the bacterial infection of the nasal-paranasal region, the present formulations may comprise a broad-spectrum antibiotic such as amoxycillin, erythromycin, or cefadroxil. Alternatively, a combination of anti-bacterial agents with differing spectra of activity may also be used. Examples of antibiotics for use in the present invention are shown in Table 3.

TABLE 3

Antibiotic Agents and Dosages

| Generic Name | Brand Name | Class | Preferable Range | More Preferable Range | Most Preferable Range | Most Preferable Dose |
|---|---|---|---|---|---|---|
| Amikacin | Amikin | aminoglycoside | 1-800 mg | 5-500 mg | 50-300 mg | 150 mg Q8H |
| Azithromycin | Zithromax | Macrolide | 25-400 mg | 75-300 mg | 150-200 mg | 167 mg Q12H |
| Aztreonan | Azactam | Monobactam | 150-1000 mg | 300-900 mg | 475-750 mg | 450 mg Q8H |
| Cefazolin | Ancef, Kefzol | Cephlasporin (Gen I) | 150-1000 mg | 300-900 mg | 575-700 mg | 650 mg Q8H |
| Cefepine | Maxipime | Cephlasporin (Gen IV) | 75-1000 mg | 200-900 mg | 575-700 mg | 650 mg Q12H |
| Cefonicid | Moniacid | Cephlasporin (Gen II) | 150-1000 mg | 300-900 mg | 575-700 mg | 600 mg Q24H |
| Cefaperazone | Cefobid | Cephlasporin (Gen III) | 150-1000 mg | 300-900 mg | 575-700 mg | 600 mg Q12H |
| Cefotaxime | Claforan | Cephlasporin (Gen III) | 150-1000 mg | 300-900 mg | 575-700 mg | 600 mg Q8-12H |
| Cefotetan | Cefotetan | Cephlasporin (Cephamycin) | 150-1000 mg | 300-900 mg | 575-700 mg | 600 mg Q8-12H |
| Cefoxitin | Mefoxin | Cephlasporin (Cephamycin) | 150-1000 mg | 300-900 mg | 575-700 mg | 600 mg Q12H |
| Ceftazidime | Fortaz, Ceptaz | Cephlasporin (Gen III) | 150-1000 mg | 300-900 mg | 475-750 mg | 550 mg Q12H |
| Ceftizoxime | Cefizox | Cephlasporin (Gen III) | 150-1000 mg | 300-900 mg | 575-700 mg | 600 mg Q8-12H |
| Ceftriaxone | Rocephin | Cephlasporin (Gen III) | 150-1000 mg | 300-900 mg | 575-700 mg | 650 mg Q12H |
| Cefuroxime | Ceftin | Cephlasporin (Gen II) | 50-600 mg | 200-520 mg | 250-400 mg | 285 mg Q8H |
| Cephapirin | Cefadyl | Cephlasporin (Gen I) | 150-1000 mg | 300-900 mg | 575-700 mg | 650 mg Q12H |
| Ciprofloxacin | Cipro | Quinolone | 15-200 mg | 50-175 mg | 750110 mg | 90 mg Q12H |
| Clindamycin | Cleocin | Lincosamide | 25-600 mg | 75-500 mg | 125-300 mg | 225 mg Q12H |
| Doxycycline | Vibramycin | Tetracycline | 10-100 mg | 15-80 mg | 25-65 mg | 27 mg Q12H |
| Erythromycin Lactobionate | Erythrocin | Macrolide | 25-600 mg | 60-350 mg | 100-300 mg | 150 mg Q8H |
| Gentamicin | Garamycin | Aminoglycoside | 1-800 mg | 5-500 mg | 50-300 mg | 150 mg Q8H |
| Kanamycin | Kantrex | Aminoglycoside | 1-800 mg | 5-500 mg | 50-300 mg | 150 mg Q8H |
| Linezolid | Zyvox | Miscellaneous | 25-600 mg | 75-450 mg | 100-300 mg | 200 mg Q12H |

TABLE 3-continued

Antibiotic Agents and Dosages

| Generic Name | Brand Name | Class | Preferable Range | More Preferable Range | Most Preferable Range | Most Preferable Dose |
|---|---|---|---|---|---|---|
| Mezlocillin | Mezlin | Penicillin | 100-1500 mg | 375-1000 mg | 750-950 mg | 833 mg Q6H |
| Mupirocin | Bactroban | Antibacterial | 1-25 mg | 1.5-20 mg | 2-15 mg | 10 mg Q6-8H |
| Nafcillin | Unipen | Penicillin | 150-1000 mg | 300-900 mg | 575-700 mg | 600 mg Q8H |
| Netilmicin | Netromycin | Aminoglycoside | 1-800 mg | 5-500 mg | 50-300 mg | 150 mg Q8H |
| Neomycin | Mycifradin | Aminoglycoside | 1-800 mg | 5-500 mg | 50-300 mg | 150 mg Q8H |
| Oxacillin | Prostaphin | Penicillin | 150-1000 mg | 300-900 mg | 575-700 mg | 600 mg Q8H |
| Paromomycin | Humatin | Aminoglycoside | 1-800 mg | 5-500 mg | 50-300 mg | 150 mg Q8H |
| Piperacillin | Pipracil | Penicillin | 50-1000 mg | 125-750 mg | 250-600 mg | 460 mg Q6H |
| Streptomycin | | Aminoglycoside | 1-800 mg | 5-500 mg | 50-300 mg | 150 mg Q8H |
| Ticarcillin + Clavulanaic | Timentin | Penicillin | 200-5000 mg | 1000-4000 mg | 1500-3500 mg | 2250 mg Q6-8H |
| Tobramycin | | Aminoglycoside | 1-800 mg | 5-500 mg | 50-300 mg | 150 mg Q8H |
| Vancomycin | Vancocin | Antibiotic-miscellaneous | 25-400 mg | 75-325 mg | 125.250 mg | 166 mg Q6-8H |

Antiviral Agents

The formulations of the present invention may comprise a therapeutically effective amount of one or more antiviral agents. These agents can be administered individually or simultaneously with the steroidal agent of the present invention. The antiviral agent may also include Acyclovir, Famciclovir, Valacyclovir, edoxudine, ganciclovir, foscarnet, cidovir (vistide), Vitrasert, Formivirsen, HPMPA (9-(3-hydroxy-2-phosphonomethoxypropyl)adenine), PMEA (9-(2-phosphonomethoxyethyl)adenine), HPMPG (9-(3-Hydroxy-2-(Phosphonomet-hoxy)propyl)guanine), PMEG (9-[2-(phosphonomethoxy)ethyl]guanine), HPMPC (1-(2-phosphonomethoxy-3-hydroxypropyl)-cytosine), ribavirin, EICAR (5-ethynyl-1-beta-D-ribofuranosylimidazole-4-carboxamine), pyrazofurin (3-[beta-D-ribofuranosyl]-4-hydroxypyrazole-5-carboxamine), 3-Deazaguanine, GR-92938X (1-beta-D-ribofuranosylpyrazole-3,4-dicarboxami-de), LY253963 (1,3,4-thiadiazol-2-yl-cyanamide), RD3-0028 (1,4-dihydro-2,3-Benzodithiin), CL387626 (4,4'-bis[4,6-d][3-aminophenyl-N-,N-bis(2-carbamoylethyl)-sulfonilimino]-1,3,5-triazin-2-ylamino-biphenyl-2-,2'-disulfonic acid disodium salt), BABIM (Bis[5-Amidino-2-benzimidazolyl]-methane), and NIH351.

Other suitable dosages and methods of treatment of the ingredients described herein are described in US 2001/0006944A1, pub. date Jul. 5, 2001, which is incorporated herein by reference in its entirety.

Other Components

The formulation of the present invention may be in any form provided the formulation can be administered to a mammal in an amount, at a frequency, and for a duration effective to prevent, reduce, or eliminate one or more symptoms associated with Rhinosinusitis, including fungus induced Rhinosinusitis. For example, a formulation within the scope of the invention can be in the form of a solid, liquid, and/or aerosol including, without limitation, powders, crystalline substances, gels pastes, ointments, salves, creams, solutions, suspensions, partial liquids, sprays, nebulae, mists, atomized vapors, tinctures, pills, capsules, tablets, and gelcaps. In addition, the formulation can contain a cocktail of other ingredients, particularly those described herein. For example, a formulation within the scope of the invention can contain, without limitation, one, two, three, four, five, or more different antifungal agents, antibiotics, antiviral agents, or the other ingredients described herein. Further, formulations within the scope of the invention can contain additional ingredients including, without limitation, pharmaceutically acceptable aqueous vehicles, pharmaceutically acceptable solid vehicles, steroids, mucolytic agents, antibacterial agents, anti-inflammatory agents, immunosuppressants, dilators, vaso-constrictors, decongestants, leukotriene inhibitors, anti-cholinergics, anti-histamines, therapeutic compounds and combinations thereof. Such antiviral agents may include IMPDH inhibitors, inhibitors of virus adsorption entry, inhibitors of fusion with host cells, antisense oligonucleotides, and nucleoside analogues.

In one embodiment, the present formulations may be provided in any form suitable for intranasal administration. In another alternative embodiment, the formulations of the present invention are in solution or suspension form suitable for intranasal administration.

In an embodiment, the formulation of the present invention may comprise a preservative, suspending agent, wetting agent, tonicity agent and/or diluent. In one embodiment, the formulations provided herein may comprise from about 0.01% to about 95%, or about 0.01% to about 50%, or about 0.01% to about 25%, or about 0.01% to about 10%, or about 0.01% to about 5% of one or more pharmacologically suitable suspending fluids which is physiologically acceptable upon administration. Pharmacologically suitable fluids for use herein include, but are not limited to, polar solvents, including, but not limited to, compounds that contain hydroxyl groups or other polar groups. Solvents include, but are not limited to, water or alcohols, such as ethanol, isopropanol, and glycols including propylene glycol, polyethylene glycol, polypropylene glycol, glycol ether, glycerol and polyoxyethylene alcohols. Polar solvents also include protic solvents, including, but not limited to, water, aqueous saline solutions with one or more pharmaceutically acceptable salt(s), alcohols, glycols or a mixture there of. In one alternative embodiment, the water for use in the present formulations should meet or exceed the applicable regulatory requirements for use in drugs.

In certain embodiments herein, the formulations of the present invention have a pH of about 2.0 to about 9.0. Optionally, the formulations of the present invention may contain a pH buffer. For example, a buffer may comprise any known pharmacologically suitable buffers which are physiologically acceptable upon administration intranasally. The buffer may be added to maintain the pH of the formulation between about 3.0 and about 7.0, for example.

Sterility or adequate antimicrobial preservation may be provided as part of the present formulations. Since certain formulations of the present invention are intended to be administered intranasally, it is preferred that they be free of pathogenic organisms. A benefit of a sterile liquid suspension is that it reduces the possibility of introducing contaminants into the individual when the suspension formulation is administered intranasally, thereby reducing the chance of an opportunistic infection. Processes which may be considered for achieving sterility may include any appropriate sterilization steps known in the art.

In one embodiment, the formulation of the present invention is produced under sterile conditions, and the micronization of the steroidal anti-inflammatory is performed in a sterile environment, and the mixing and packaging is conducted under sterile conditions. In one alternative embodiment, one or more ingredients in the present formulation may be sterilized by steam, gamma radiation or prepared using or mixing sterile steroidal powder and other sterile ingredients where appropriate. Also, the formulations may be prepared and handled under sterile conditions, or may be sterilized before or after packaging.

In addition to or in lieu of sterilization, the formulations of the present invention may contain a pharmaceutically acceptable preservative to minimize the possibility of microbial contamination. Additionally, a pharmaceutically-acceptable preservative may be used in the present formulations to increase the stability of the formulations. It should be noted, however, that any preservative must be chosen for safety, as the treated tissues may be sensitive to irritants. Preservatives suitable for use herein include, but are not limited to, those that protect the solution from contamination with pathogenic particles, including phenylethyl alcohol, benzalkonium chloride, benzoic acid, or benzoates such as sodium benzoate. Preferably, the preservative for use in the present formulations is benzalkonium chloride or phenylethyl alcohol. In certain embodiments, the formulations herein comprise from about 0.01% and about 1.0% w/w of benzalkonium chloride, or from about 0.01% and about 1% v/w phenylethyl alcohol. Preserving agents may also be present in an amount from about 0.01% to about 1%, preferably about 0.002% to about 0.02% by total weight or volume of the formulation.

The formulations provided herein may also comprise from about 0.01% to about 90%, or about 0.01% to about 50%, or about 0.01% to about 25%, or about 0.01% to about 10%, or about 0.01% to about 1% w/w of one or more emulsifying agent, wetting agent or suspending agent. Such agents for use herein include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methylcellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyltartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of polycondensed fatty acids of castor oil; propane-1,2-diol esters of fatty acids; sodium stearoyl-2lactylate; calcium stearoyl-2-lactylate; stearoyl tartrate; sorbitan monostearate; sorbitan tristearate; sorbitan monolaurate; sorbitan monooleate; sorbitan monopalmitate; extract of quillaia; polyglycerol esters of dimerised fatty acids of soya bean oil; oxidatively polymerised soya bean oil; and pectin extract. In certain embodiments herein, the present formulations comprise polysorbate 80, microcrystalline cellulose, carboxymethylcellulose sodium and/or dextrose.

The present formulations may further comprise from about 0.01% to about 90%, or about 0.01% to about 50%, or about 0.01% to about 25%, or about 0.01% to about 10%, or about 0.01% to about 1% w/w of one or more excipients and additives which are pharmacologically suitable. Excipients and additives generally have no pharmacological activity, or at least no undesirable pharmacological activity. The concentration of these may vary with the selected agent, although the presence or absence of these agents, or their concentration is not an essential feature of the invention. The excipients and additives may include, but are not limited to, surfactants, moisturizers, stabilizers, complexing agents, antioxidants, or other additives known in the art. Complexing agents include, but are not limited to, ethylenediaminetetraacetic acid (EDTA) or a salt thereof, such as the disodium salt, citric acid, nitrilotriacetic acid and the salts thereof. In another embodiment, particularly in the suspension formulations provided herein, the complexing agent is sodium edetate. In one embodiment, the compositions contain sodium edetate at a concentration of about 0.05 mg/mL to about 0.5 mg/mL, or about 0.1 mg/mL to about 0.2 mg/mL. Also, for example, the formulations of the present invention may comprise from about 0.001% to about 5% by weight of a humectant to inhibit drying of the mucous membrane and to prevent irritation. Any of a variety of pharmaceutically-acceptable humectants can be employed, including sorbitol, propylene glycol, polyethylene glycol, glycerol or mixtures thereof, for example.

The formulations provided herein also may comprise about 0.01% to about 90%, or about 0.01% to about 50%, or about 0.01% to about 25%, or about 0.01% to about 10%, or about 0.01% to about 10% w/w of one or more solvents or co-solvents to increase the solubility of any of the components of the present formulations. Solvents or co-solvents for use herein include, but are not limited to, hydroxylated solvents or other pharmaceutically-acceptable polar solvents, such as alcohols including isopropyl alcohol, glycols such as propylene glycol, polyethylene glycol, polypropylene glycol, glycol ether, glycerol, and polyoxyethylene alcohols. In another embodiment, the formulations of the present invention may comprise one or more conventional diluents known in the art. The preferred diluent is purified water.

Tonicity agents may include, but are not limited to, sodium chloride, potassium chloride, zinc chloride, calcium chloride and mixtures thereof. Other osmotic adjusting agents may also include, but are not limited to, mannitol, glycerol, and dextrose or mixtures thereof. In an alternative embodiment, the present formulation may comprise about 0.01% to about 10% w/w, or about 1% to about 8% w/w, or 1% to about 6% w/w, preferably about 5.0% w/w. The preferred tonicity agent is anhydrous dextrose.

In one alternative embodiment, the formulations of the present invention are stable. As used herein, the stability of formulations provided herein refers to the length of time at a given temperature that greater than 80%, 85%, 90% or 95% of the initial amount of the active ingredients is present in the formulation. For example, the formulations provided herein may be stored between about 15° C. and about 30° C., and remain stable for at least 1, 2, 12, 18, 24 or 36 months. Also, the formulations may be suitable for administration to a subject in need thereof after storage for more than 1, 2, 12, 18, 24 or 36 months at 250. Also, in another alternative embodiment, using Arrhenius Kinetics, more than 80%, or more than 85%, or more than 90%, or more than 95% of the initial amount of active ingredients remains after storage of the formulations for more than 1, 2, 12, 18, 24 or 36 months between about 15° C. and about 30° C.

The formulations of the present invention may be manufactured in any conventional manner known in the art, or by minor modification of such means. For example, the formulations may be manufactured by thoroughly mixing the ingredients described herein at ambient or elevated temperatures in order to achieve solubility of ingredients where appropriate.

The preparation of the steroidal inflammatory of the present invention, e.g., fluticasone propionate and beclomethasone dipropionate, having a specific particle size distribution profile may be obtained by any conventional means known in the art, or by minor modification of such means. For example, suspensions of drug particles can rapidly undergo particulate size reduction when subjected to "jet milling" (high pressure particle in liquid milling) techniques. Other known methods for reducing particle size into the micrometer range include mechanical milling, the application of ultrasonic energy and other techniques.

In addition, the formulations of the present invention may comprise any of the following components: (i) antihistamine: (ii) non-steroidal anti-flammatories; (iii) decongestants; (iv) mucolytics; (v) anticholinergics; or (vi) mass cell stabilizers. Examples of such components are found in U.S. 2002/0061281 A1, published May 23, 2002. This reference is incorporated herein by reference in its entirety.

In one alternative embodiment, the present invention is directed to a pharmaceutical composition that may be useful in treating rhinosinusitis caused by Alpha Hemolytic Sreptococci, Beta Hemolytic Streptococci, Branhamella Catarrhalis, Diptheroids, Heaemophilis influenza (beta-lactamase positive and negative), *Moraxella species, Psuedomonas aeroguinosa, Pseudomas maltophilia, Serratia marcesns, Staphylococcus aureus, Streptococcus pheumonia, Aspergillosis, Mucor* and *Candida albicans, Flusarium, Curvularia, crytococcus, coccidiodes*, and *histoplasma*.

Mode of Administration

Administration of the present formulations can be any type of administration that places the present formulations in contact with nasal-paranasal mucosa. Direct intranasal administration includes, without limitation, nasal irrigations, nasal sprays, nasal inhalations, and nasal packs with, for example, saturated gauze provided the administered agent contacts nasal-paranasal mucosa prior to crossing epithelium. In addition, injections into the nasal-paranasal cavities using, for example, a needle or catheter tube is considered a direct intranasal administration provided the administered agent contacts nasal-paranasal mucosa after leaving the needle or catheter tube and prior to crossing epithelium. Any device can be used to directly administer the present formulations intranasally including, without limitation, a syringe, bulb, inhaler, canister, spray can, nebulizer, and mask.

Indirect administration to the nasal-paranasal anatomies can include, without limitation, oral, intravenous, intradermal, and intraperitoneal administrations provided the administered agent contacts nasal-paranasal mucosa. In addition, any device can be used to indirectly administer an agent to the nasal-paranasal anatomy including, without limitation, a syringe and regulated release capsule.

The present formulations may be packaged in any conventional manner suitable for administration of the present formulations. Spray administration containers for various types of nasal formulations have been known in the past and substantially all will be equally suitable for the present formulations, provided that the container materials is compatible with the formulation. In an embodiment, the formulation of the present invention herein is packaged in a container such that it can be dispersed as a mist to be directed into each nostril. For example, the container may be made of flexible plastic such that squeezing the bottle's sides impels the spray out through the nozzle into the nasal cavity. Alternatively, a small pump button may pump air into the container and cause the liquid spray to be emitted on the return stroke when pressed.

In an alternative embodiment, the formulations of the present invention are packaged in a container pressurized with a gas which is inert to the user and to the ingredients of the solution. The gas may be dissolved under pressure in the container or may be generated by dissolution or reaction of a solid material which forms the gas as a product of dissolution or as a reaction product. Suitable inert gases which can be used herein include nitrogen, argon, and carbon dioxide. Also, the formulations herein may be administered as a spray or aerosol wherein the formulation is packaged in a pressurized container with a liquid propellant such as dicholorodifluoro methane or chlorotrifluoro ethylene, or other propellant.

Preferably, the present formulations are packaged in a metered dose spray pump, or metering atomizing pump, such that each actuation of the pump delivers a fixed volume of the formulation (i.e. per spray-unit). For administration in drop or other topical form, the formulations herein may suitably be packaged in a container provided with a conventional dropper/closure device, comprising a pipette or the like, preferably delivering a substantially fixed volume of the formulation.

Method of Treatment

The present invention is also directed to a method for treating rhinosinusitis, including fungus-induced rhinosinusitis. In one embodiment, the method of treating rhinosinusitis of the present invention comprises the step of administering a therapeutically effective amount of the formulation of the present invention to a mammal in need thereof. The formulation may comprise the steroidal agent of the present invention alone or in combination with an anti-fungal agent, an antibiotic or antiviral agent. The formulation is preferably administered intranasally. In one embodiment, the formulation is administered directly to the nasal-paranasal mucosa. In an alternative embodiment, the formulation is administered intranasally via a metered dose spray pump. In general, the course of treatment for any individual with respect to any of the active ingredients described herein can be readily determined by his or her physician.

The method of the present invention may further comprise administering the formulation of the present for a duration or frequency sufficient to treat one or more symptoms of rhinosinusitis, including fungus-induced rhinosinusitis. For example, the formulation may be administered one time to about 10 times a day for about one day to about 100 days or more, or until such fungus-induced rhinosinusitis is treated. In an embodiment, the method of the present invention comprises administering to a mammal diagnosed with fungus-induced rhinosinusitis a formulation comprising a therapeutically effective amount of an antifungal agent and a steroidal anti-inflammatory intranasally via a metered dose spray pump one to three times a day for up to two weeks. In an alternative embodiment, the administration of the present formulations may comprise 1, 2, 3, 4, 5, 6, 7 or 8 applications of the present formulation to the nasal-paranasal mucosa one, two, three, four or five times a day.

In an alternative embodiment, the formulation of the method of the present invention further comprises an antibiotic. However, when administering antibiotics, physicians must keep in mind the incidence of drug-resistant bacteria in their community and consider the patient's overall health status. Special attention should be given to diseases that could impede normal recovery from infection and/or predispose to complications (e.g., diabetes mellitus, chronic pulmonary disease, asthma, cystic fibrosis and immune deficiencies). Additionally, physicians should consider whether or not the patient is immunocomprimised in selecting an antibiotic. In one embodiment, the antibiotic is administered for a period of 1 day to about 10 weeks. In an alternative embodiment, the antibiotic is administered for about 1 day to about 28 days.

Accordingly, the present invention provides a method of treating fungus-induced rhinosinusitis associated with a bacterial infection in the nasal-paranasal region, comprising the steps of administering a formulation comprising an antifungal agent, steroidal anti-inflammatory, and antibiotic until said bacterial infection is cured, and then administering a formulation comprising an antifungal agent and steroidal anti-inflammatory.

In an alternative embodiment, the present invention provides a method of treating fungus-induced rhinosinusitis, comprising the steps of administering a formulation comprising a steroidal anti-inflammatory alone or in combination or in conjunction with an antifungal agent, antibiotic or antiviral agent. For example, the steroidal agent may be administered separately from the antifungal agent or antibiotic, or each ingredient can be administered simultaneously (e.g., in a single formulation) concurrently, subsequently, or in tandem. In another embodiment, each ingredient is administered individually in its own formulation and pursuant to an appropriate dosage regimen for that particular ingredient. Suitable dosage regimens for steroidal agents, fungal agents, antibiotics or antiviral agents are known by those skilled in the art.

EXAMPLES

Examples 1-5 herein are prophetic examples provided to illustrate, but not to limit, the formulations and methods of the present invention. They are presented with the understanding that changes can be and may need to be made to a specific composition in order to obtain or optimize the formulation. Such modifications to the following prophetic examples, if needed, are normal and understandable to those of ordinary skill in the art, and shall not be used to limit the invention.

It is believed that prophetic examples 1-5 would be suitable for administration to the nasal-paranasal mucosa of an individual suffering from fungus-induced rhinosinusitis associated with a bacterial infection. The formulations may be sterile. It is understood that the steroid, antibiotic, antifungal agent or the other ingredients described herein may be administered in the same formulation, or may be administered individually, or in any combination thereof.

Example 1

| | |
|---|---|
| Amphotericin B | 2.0-100.0 mg/ml |
| Neomycin Sulfate | 5.0-100.0 mg/ml |
| Phenylethyl Alcohol | 0.5-10.0 mg.ml |
| Fluticasone Propionate | 0.25-1.0 mg/ml |
| Microcrystalline Cellulose | 5.0-15.0 mg/ml |
| Polysorbate | 80 0.1-1.0 mg/ml |
| Purified Water | q.s. |

Example 1 is a prophetic example of a formulation of the present invention, wherein about 10% of the fluticasone propionate particles have a particle size of less than 0.70 microns; about 25% of the fluticasone propionate particles have a particle size of less than 1.30 microns; about 50% of the fluticasone propionate particles have a particle size of less than 2.5 microns; about 75% of the fluticasone propionate particles have a particle size of less than 4.0 microns; about 90% of the fluticasone propionate particles have a particle size of less than 6.0 microns; and greater than 90% or about 100% of the fluticasone propionate particles have a particle size of less than 10 microns. The solution of Example 1 may be made by methods known to those of ordinary skill in the art.

Example 2

| | |
|---|---|
| Fluconazole | 1.0-20.0 mg/ml |
| Neomycin Sulfate | 5.0-100.0 mg/ml |
| Phenylethyl Alcohol | 0.5-10.0 mg/ml |
| Fluticasone Propionate | 0.25-1.0 mg/ml |
| Microcrystalline Cellulose | 5.0-15.0 mg/ml |
| Polysorbate | 80 0.1-1.0 mg/ml |
| Purified Water | q.s. |

Example 2 is a prophetic example of a formulation of the present invention, wherein about 10% of the fluticasone propionate particles have a particle size of less than 0.70 microns; about 25% of the fluticasone propionate particles have a particle size of less than 1.30 microns; about 50% of the fluticasone propionate particles have a particle size of less than 2.5 microns; about 75% of the fluticasone propionate particles have a particle size of less than 4.0 microns; about 90% of the fluticasone propionate particles have a particle size of less than 6.0 microns; and greater than 90% or about 100% of the fluticasone propionate particles have a particle size of less than 10 microns. The solution of Example 2 may be made by methods known to those of ordinary skill in the art.

Example 3

| | |
|---|---|
| Amphotericin B | 2.0-100.0 mg/ml |
| Neomycin Sulfate | 5.0-100.0 mg/ml |
| Benzalkonium Chloride | 0.1-0.5 mg/ml |
| Dextrose | 20.0-100.0 |
| Phenylethyl Alcohol | 0.5-10.0 mg.ml |
| Beclomethasone Dipropionate | 0.25-1.0 mg/ml |
| Purified Water | q.s. |

Example 3 is a prophetic example of a formulation of the present invention, wherein about 10% of the beclomethasone dipropionate particles have a particle size less than 0.40 microns; about 25% of the beclomethasone dipropionate particles have a particle size less than 0.70 microns; about 50% of the beclomethasone dipropionate particles have a particle size less than 1.3 microns; about 75% of the beclomethasone dipropionate particles have a particle size less than 2.0 microns; about 90% of the beclomethasone dipropionate particles have a particle size less than 3.0 microns; and greater than 90% or about 100% of the beclomethasone dipropionate particles have a particle size less than 6.0 microns. Example 3 may be made by methods known to those of ordinary skill in the art.

Example 4

| | |
|---|---|
| Fluconazole | 1.0-20.0 mg/ml |
| Neomycin Sulfate | 5.0-100.0 mg/ml |
| Benzalkonium Chloride | 0.1-0.5 mg/ml |
| Dextrose | 20.0-100.0 |
| Phenylethyl Alcohol | 0.5-10.0 mg.ml |
| Beclomethasone Dipropionate | 0.25-1.0 mg/ml |
| Purified Water | q.s. |

Example 4 is a prophetic example of a formulation of the present invention, wherein about 10% of the beclomethasone dipropionate particles have a particle size less than 0.40 microns; about 25% of the beclomethasone dipropionate particles have a particle size less than 0.70 microns; about 50% of the beclomethasone dipropionate particles have a particle size less than 1.3 microns; about 75% of the beclomethasone dipropionate particles have a particle size less than 2.0 microns; about 90% of the beclomethasone dipropionate particles have a particle size less than 3.0 microns; and greater than 90% or about 100% of the beclomethasone dipropionate particles have a particle size less than 6.0 microns. Example 4 may be made by methods known to those of ordinary skill in the art.

Example 5

| | |
|---|---|
| Fluconazole | 1.0-20.0 mg/ml |
| Benzalkonium Chloride | 0.1-0.5 mg/ml |
| Dextrose | 20.0-100.0 |
| Phenylethyl Alcohol | 0.5-10.0 mg.ml |
| Beclomethasone Dipropionate | 0.25-1.0 mg/ml |
| Purified Water | q.s. |

Example 5 is a prophetic example of a formulation of the present invention, wherein about 10% of the beclomethasone dipropionate particles have a particle size less than 0.40 microns; about 25% of the beclomethasone dipropionate particles have a particle size less than 0.70 microns; about 50% of the beclomethasone dipropionate particles have a particle size less than 1.3 microns; about 75% of the beclomethasone dipropionate particles have a particle size less than 2.0 microns; about 90% of the beclomethasone dipropionate particles have a particle size less than 3.0 microns; and greater than 90% or about 100% of the beclomethasone dipropionate particles have a particle size less than 6.0 microns. Example 5 may be made by methods known to those of ordinary skill in the art.

The Examples herein are presented for illustrative purposes only. They are not intended to limit the scope of the invention. Further, it should be understood that various changes and modifications to the embodiment described herein will be apparent to those skilled in the art. Such changes and modifications can be made without departing from the spirit and scope of the present invention and without diminishing its attendant advantages. It is therefore intended that such changes and modifications be covered by the appended claims. Also, the invention may suitably comprise, consist of or consist essentially of the elements or steps described herein. Further, the invention described herein suitably may comprise or be practiced in the absence of any element or step which is not specifically disclosed herein. Further, one or more step described herein may be performed simultaneously with another step.

What is claimed is:

1. A formulation for the treatment of fungus-induced rhinosinusitis in a mammal, said formulation comprising an aqueous suspension comprising:
    a) 0.04% to 0.06% by weight of a suspended solid steroidal anti-inflammatory, wherein the steroidal anti-inflammatory is fluticasone or a pharmaceutically acceptable salt, ester, enol ether, enol ester, acid, or base thereof, said suspended solid steroidal anti-inflammatory having the following particle size distribution profile:
        i. about 10% of the steroidal anti-inflammatory particles have a particle size of less than 0.4 microns;
        ii. about 25% of the steroidal anti-inflammatory particles have a particle size of less than 0.8 microns;
        iii. about 50% of the steroidal anti-inflammatory particles have a particle size of less than 1.5 microns;
        iv. about 75% of the steroidal anti-inflammatory particles have a particle size of less than 3.0 microns; and
        v. about 90% of the steroidal anti-inflammatory particles have a particle size of less than 5.3 microns; wherein said formulation is suitable for administration to the nasal-paranasal mucosa;
    b) from about 0.5 to 150 mg of an antifungal agent; and
    c) at least at least one complexing agent selected from the group consisting of ethylenediaminetetraacetic acid, citric acid, nitrilotriacetic acid, salts thereof, and sodium edetate.

2. The formulation of claim 1, wherein the steroidal anti-inflammatory is fluticasone propionate wherein;
    greater than 90% or about 100% of the fluticasone propionate particles have a particle size of less than 10 microns.

3. The formulation of claim 1, wherein the aqueous suspension is deliverable via an atomizing device.

4. The formulation of claim 3, wherein the formulation is disposed in a metered dose spray pump.

5. The formulation of claim 1, further comprising about 20 to about 70 mg of fluconazole or itraconazole.

6. The formulation of claim 5, wherein the formulation comprises about 25 to about 50 mg of fluconazole or itraconazole.

7. The formulation of claim 6, wherein the formulation comprises about 30 mg of fluconazole or itraconazole.

8. The formulation of claim 5, wherein the formulation comprises about 7.5 to about 15 mg of amphotericin β.

9. The formulation of claim 1, further comprising an antibiotic, antiviral agent, or combinations thereof.

10. The formulation of claim 9, wherein the antibiotic is one or more of amikacin, azithromycin, aztreonan, cefazolin, cefepine, cefonicid, cefaperazone, cefotaxime, cefotetan, cefoxitin, ceftazidime, ceftizoxime, ceftriaxone, cefuroxime, Cephapirin, ciprofloxacin, clindamycin, doxycycline, erythromycin lactobionate, gentamicin, kanamycin, linezolid, mezlocillin, mupirocin, nafcillin, netilmicin, neomycin, oxacillin, paromomycin, piperacillin, streptomycin, ticarcillin, tobramycin, or vancomycin.

11. The formulation of claim 1, wherein the formulation is a sterile aqueous suspension.

12. The formulation of claim 1, wherein the at least one complexing agent is sodium edetate.

13. The formulation of claim 1, wherein said formulation is sterile and has a relatively long period of stability such that after storage for 12 months at a temperature between 15 to 30° C., greater than 90% of the mometasone originally present in the formulation still remains in the formulation.

14. The formulation of claim 1, wherein the antifungal agent is amphotericin β, fluconazole, itraconazole, or combinations thereof.

15. The formulation of claim 1, further comprising neomycin sulfate.

16. A nasal spray formulation comprising:
an aqueous suspension having
a) 0.04% to 0.05% by weight of a suspended solid steroidal anti-inflammatory, wherein the suspended solid steroidal anti-inflammatory is beclomethasone or a pharmaceutically acceptable salt, ester, enol ether, enol ester, acid, or base thereof having the following particle size distribution profile:
   i. about 10% of the steroidal anti-inflammatory particles have a particle size of less than 0.3 microns;
   ii. about 25% of the steroidal anti-inflammatory particles have a particle size of less than 0.6 microns;
   iii. about 50% of the steroidal anti-inflammatory particles have a particle size of less than 1.1 microns;
   iv. about 75% of the steroidal anti-inflammatory particles have a particle size of less than 1.8 microns; and
   v. about 90% of the steroidal anti-inflammatory particles have a particle size of less than 2.7 microns; wherein said formulation is suitable for administration to the nasal-paranasal mucosa;
b) from about 0.5 to 150 mg of an antifungal agent; and
c) at least at least one complexing agent selected from the group consisting of ethylenediaminetetraacetic acid, citric acid, nitrilotriacetic acid, salts thereof, and sodium edetate.

17. The nasal spray formulation of claim 16, wherein the formulation is disposed in a metered dose spray pump and further comprises about 10 to about 100 mg of doxycyline and a therapeutic amount of an antiviral agent selected from the group consisting of Acyclovir, Famciclovir, Valacyclovir, edoxudine, ganciclovir, foscarnet, cidofovir (vistide), Vitrasert and Formivirsen.

18. The nasal spray formulation according to claim 17, wherein the formulation is disposed in a metered dose spray pump and further comprising ambient air as the propelling agent for delivering each spray of the metered-dose spray pump.

19. The nasal spray formulation of claim 16, further comprising a preservative, suspending agent, wetting agent, buffer, diluent, or combinations thereof.

20. The nasal spray formulation of claim 16, wherein the formulation further comprises one or more of the following compounds: (a) microcrystalline cellulose; (b) carboxymethyl cellulose sodium; (c) dextrose; (d) benzalkonium chloride; (e) polysarbate 80; or (f) phenylethyl alcohol.

21. The nasal spray formulation of claim 16, wherein the antifungal agent is mphotericin β, fluconazole, itraconazole, or combinations thereof.

22. The nasal spray formulation of claim 16, wherein said formulation is sterile and has a relatively long period of stability such that after storage for 12 months at a temperature between 15 to 30° C., greater than 90% of the beclomethasone originally present in the formulation still remains in the formulation.

23. The formulation of claim 16, wherein the at least one complexing agent is sodium edetate.

24. The formulation of claim 16, wherein the antifungal agent is amphotericin β, fluconazole, itraconazole, or combinations thereof.

25. The formulation of claim 16, further comprising neomycin sulfate.

26. A method of treating fungus-induced rhinosinusitis in a mammal, said method comprising the steps of applying to the mammal's nasal-paranasal mucosa a formulation according to claim 16 in each nostril of the mammal for 9 to 14 days.

27. The method of claim 26, wherein the antifungal agent is amphotericin β, fluconazole, itraconazole, or combinations thereof.

28. The method of claim 26, formulation is applied via a metered-dose, manual pump spray unit.

29. A method of treating fungus-induced rhinosinusitis in a mammal, said method comprising the steps of applying to the mammal's nasal-paranasal mucosa a formulation according to claim 1 in each nostril of the mammal for 9 to 14 days.

30. The method of claim 29, wherein the antifungal agent is amphotericin β, fluconazole, itraconazole, or combinations thereof.

31. The method of claim 29, formulation is applied via a metered-dose, manual pump spray unit.

32. The method of claim 31, wherein the formulation is administered to the mammal as one spray in each nostril from 1 to about 10 times per day.

33. The method of claim 29, wherein the formulation further comprises at least at least one complexing agent selected from the group consisting of ethylenediaminetertraacetic acid, citric acid, nitrilotriacetic acid, salts thereof, and sodium edetate.

34. The method of claim 33, wherein the at least on complexing agent is sodium edetate.

35. The method of claim 29, wherein said formulation is sterile and has a relatively long period of stability such that after storage for 12 months at a temperature between 15 to 30° C., greater than 90% of the beclomethasone originally present in the formulation still remains in the formulation.

* * * * *